US00PP23028P2

(12) United States Plant Patent
Bergman

(10) Patent No.: US PP23,028 P2
(45) Date of Patent: Sep. 11, 2012

(54) ***CHRYSANTHEMUM* PLANT NAMED 'CIDZ0003'**

(50) Latin Name: *Chrysanthemum×morifolium*
Varietal Denomination: CIDZ0003

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/135,912

(22) Filed: Jul. 18, 2011

(51) Int. Cl.
*A01H 5/00* (2006.01)

(52) U.S. Cl. ..... Plt./289

(58) Field of Classification Search ..... Plt./289
See application file for complete search history.

*Primary Examiner* — Kent L Bell
(74) *Attorney, Agent, or Firm* — Joshua L. Price

(57) ABSTRACT

A new *Chrysanthemum* plant named 'CIDZ0003' particularly distinguished by the rich, deep yellow ray floret color that has excellent color retention in heat, dark green foliage, a seven week flowering response time, and is suitable for production as a disbudded plant or with no bud removal.

1 Drawing Sheet

Latin name of the genus and species of the plant claimed: *Chrysanthemum×morifolium.*

Varietal denomination: 'CIDZ0003'.

BACKGROUND OF THE NEW PLANT

The present invention comprises a new *Chrysanthemum*, botanically known as *Chrysanthemum×morifolium*, and hereinafter referred to by the variety name 'CIDZ0003'.

'CIDZ0003' is a product of a planned breeding program. The new cultivar has rich, deep yellow ray floret color that has excellent color retention in heat, dark green foliage, a seven week flowering response time, and is suitable for production as a disbudded plant or with no bud removal.

'CIDZ0003' originated from a hybridization made in May 2005 in a controlled breeding environment in Salinas, Calif., USA. The female parent was the proprietary plant designated 'YB-A7604', unpatented, with yellow ray floret color, more compact growth habit, and a week slower flowering response time.

The male parent of 'CIDZ0003' was an unpatented plant identified as 'YB-A5705' with yellow ray floret color, medium vigor, a more open inflorescence center with pollen, and a slower flowering response time. The resultant seed was sown in October 2005 in Fort Myers, Fla., USA.

'CIDZ0003' was selected as one flowering plant within the progeny of the stated cross in February 2006 in a controlled environment in Fort Myers, Fla., USA.

The first act of asexual reproduction of 'CIDZ0003' was accomplished when vegetative cuttings were propagated from the initial selection in March 2006 in a controlled environment in Fort Myers, Fla., USA.

BRIEF SUMMARY OF INVENTION

Horticultural examination of plants grown from cuttings of the plant initiated in March 2006, and continuing thereafter, has demonstrated that the combination of characteristics as herein disclosed for 'CIDZ0003' are firmly fixed and are retained through successive generations of asexual reproduction.

'CIDZ0003' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7061). 'CIDZ0003' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIDZ0003' with colors being as true as possible with an illustration of this type. The photographic drawing shows four flowering potted plants of the new variety and a close-up of the inflorescence.

DETAILED BOTANICAL DESCRIPTION

The plant descriptions, measurements and aforementioned photographs were taken in Gilroy, Calif. in early May 2011 under natural light. These plants were propagated and grown in Nipomo, Calif. and shipped to Gilroy, Calif. for the data collection and photographs. These plants were approximately 11 weeks of age; grown as four plants together in a six inch pot under greenhouse trial conditions.

Color references are made to The Royal Horticultural Society Colour Chart (R.H.S.) 2001.

TABLE 1

DIFFERENCES BETWEEN THE NEW VARIETY 'CIDZ0003' AND A SIMILAR VARIETY

| | 'CIDZ0003' | 'Yocovington' (U.S. Plant Pat.No. 13,031) |
|---|---|---|
| Ray floret color: | Deeper yellow | Not as deep yellow |
| Ray floret length: | Bit shorter | Longer |

TABLE 1-continued

DIFFERENCES BETWEEN THE NEW VARIETY 'CIDZ0003' AND A SIMILAR VARIETY

| | 'CIDZ0003' | 'Yocovington' (U.S. Plant Pat.No. 13,031) |
|---|---|---|
| Ray floret under-surface color: | More yellow | Lighter yellow |
| More open centered inflorescence form when grown in the winter months: | No | Yes |
| Petiole color: | Darker | Lighter |

Plant:

*Form, growth and habit*.—Herbaceous pot type, stems upright, strong and moderately vigorous growth habit.

*Plant height*.—20-22.0 cm.

*Plant height* (*inflorescence included*).—27-30.0 cm.

*Plant width*.—16-18.0 cm.

Roots:

*Number of days to initiate roots*.—4 days at about 22 degrees C.

*Number of days to produce a rooted cutting*.—About 10 days at 22 degrees C.

*Type*.—Fine, fibrous, free branching.

*Color*.—RHS N155B but whiter.

Foliage:

*Arrangement*.—Alternate, simple.

*Immature, leaf color, upper surface*.—RHS 137A but slightly darker.

*Lower surface*.—RHS 137C.

*Mature, leaf color, upper surface*.—RHS 137A but slightly darker.

*Lower surface*.—RHS 137C.

*Length*.—8.2-9.0 cm.

*Width*.—5.9-6.9 cm.

*Shape*.—Ovate.

*Base shape*.—Attenuate.

*Apex shape*.—Slightly mucronulate.

*Margin*.—Palmately lobed; slightly and softly serrate.

*Texture, upper surface*.—Bifid T-shaped hairs.

*Lower surface*.—Bifid T-shaped hairs.

*Color of veins, upper surface*.—RHS 144A.

*Color of veins, lower surface*.—RHS 144A.

*Petiole color*.—RHS 144A.

*Length*.—2.6-3.4 cm.

*Diameter*.—0.3-0.35 cm.

*Texture*.—Bifid T-shaped hairs.

Stem:

*Quantity of main branches per plant*.—4-5.

*Color of stem*.—RHS 137B but appears lighter due to hairs.

*Length of stem*.—24-26.0 cm.

*Diameter*.—0.5-0.6 cm.

*Length of internodes*.—2.5-3.0 cm.

*Texture*.—Bifid T-shaped hairs.

*Color of peduncle*.—RHS 137B but appears lighter due to hairs.

*Length of peduncle*.—3.0-4.0 cm.

*Peduncle diameter*.—0.4 cm.

*Texture*.—Bifid T-shaped hairs.

Inflorescence:

*Type*.—Compositae type, solitary inflorescences, decorative-type, borne terminally above foliage, ray florets arranged acropetally on a capitulum.

*Quantity of short days to flowering* (*response time*).—Approximately 7 weeks.

*Quantity of inflorescences per plant*.—5-6.

*Lastingness of individual blooms on the plant*.—About 4 weeks.

*Fragrance*.—Slightly spicy.

Bud (just when opening/showing color):

*Color*.—RHS 5B.

*Length*.—1.3-1.5 cm.

*Width*.—1.3-1.4 cm.

*Shape*.—Oblate.

Immature inflorescence:

*Diameter*.—8.0 cm.

*Color of ray florets, upper surface*.—Closest to RHS 5A but deeper.

*Lower surface*.—RHS 5B.

Mature inflorescence:

*Diameter*.—10.4-11.3 cm.

*Depth*.—3.6-4.0 cm.

*Total diameter of 'disc'*.—Visually indistinct.

*Receptacle height*.—0.5-0.7 cm.

*Receptacle diameter*.—0.9-1.1 cm.

Ray florets:

*Average quantity of florets*.—Approximately 200 in numerous whorls.

*Color of florets, upper surface*.—RHS 5A.

*Lower surface*.—RHS 6C.

*Length*.—4-5.7 cm.

*Width*.—0.8-1.2 cm.

*Shape*.—Slightly elliptical to narrowly oblanceolate.

*Apex shape*.—Irregularly retuse.

*Margin*.—Entire.

*Texture, upper surface*.—Papillose.

*Lower surface*.—Papillose.

Disc florets:

*Average quantity of florets*.—1-3.

*Color of florets*.—RHS 155C with RHS 4A apex.

*Length*.—0.5 cm.

*Width*.—0.1 cm.

*Shape*.—Tubular, elongated.

*Apex shape*.—Acute, 5 pointed.

Phyllaries:

*Quantity*.—Approximately 30 in numerous whorls.

*Color, upper surface*.—Closest to RHS 137C.

*Lower surface*.—Between RHS 137B to RHS 137C.

*Length*.—0.6-0.9 cm.

*Width*.—0.2-0.5 cm.

*Shape*.—Broadly lanceolate to ovate.

*Apex shape*.—Acute.

*Base*.—Fused.

*Margins*.—Entire, with RHS N199B edges; some margins papery.

*Texture, upper surface*.—Glabrous.

*Lower surface*.—Bifid T-shaped hairs.

Reproductive organs:

*Pistil*.—1.

*Found on both florets*.—Yes.

*Length*.—0.7 cm.

*Style color*.—RHS 1C.

*Style length*.—0.6 cm.

*Stigma color*.—RHS 9A.

*Stigma shape*.—Bi-parted.
*Ovary color*.—Not observed.
*Stamens*.—4.
*Found on only disc florets*.—Yes.
*Color of filaments*.—RHS 1C.
*Length filaments*.—0.2 cm.
*Anther color*.—Too dried out; therefore not observed.
*Anther length*.—Not observed.
*Anther shape*.—Not observed.
*Color of pollen*.—Not observed.
*Pollen amount*.—Not observed.
*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'CIDZ0003' substantially as illustrated and described herein.

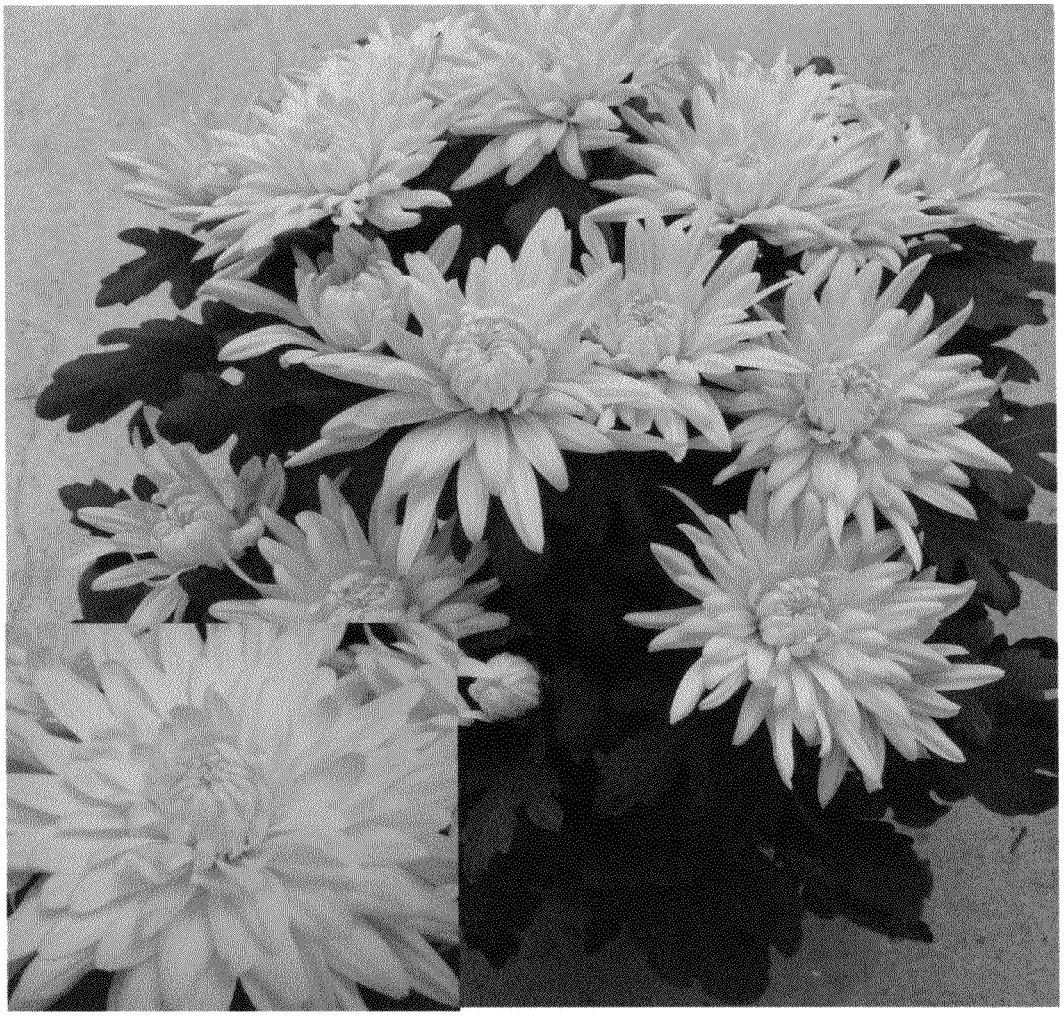

* * * * *